(12) United States Patent
Jackson et al.

(10) Patent No.: US 10,335,774 B2
(45) Date of Patent: Jul. 2, 2019

(54) CARBONYLATION PROCESS AND CATALYST SYSTEM THEREFOR

(71) Applicant: JOHNSON MATTHEY DAVY TECHNOLOGIES LIMITED, London (GB)

(72) Inventors: Simon Wayne Jackson, Durham (GB); Adam Armour Snaith, Durham (GB); Michael William Marshall Tuck, London (GB); David John Watson, Durham (GB)

(73) Assignee: Johnson Matthey Davy Technologies Limited, London (GB)

( * ) Notice: Subject to any disclaimer, the term of this patent is extended or adjusted under 35 U.S.C. 154(b) by 0 days.

(21) Appl. No.: 15/564,867

(22) PCT Filed: Mar. 24, 2016

(86) PCT No.: PCT/GB2016/050860
§ 371 (c)(1),
(2) Date: Oct. 6, 2017

(87) PCT Pub. No.: WO2016/162663
PCT Pub. Date: Oct. 13, 2016

(65) Prior Publication Data
US 2018/0104673 A1   Apr. 19, 2018

(30) Foreign Application Priority Data
Apr. 8, 2015 (GB) .................................. 1505977.7

(51) Int. Cl.
*B01J 27/02* (2006.01)
*B01J 21/08* (2006.01)
(Continued)

(52) U.S. Cl.
CPC ............... *B01J 27/02* (2013.01); *B01J 21/08* (2013.01); *B01J 35/1019* (2013.01);
(Continued)

(58) Field of Classification Search
CPC ................ B01J 35/1019; B01J 35/1023; B01J 35/1038; B01J 35/1042; B01J 35/1061; B01J 27/02; B01J 21/08; C07C 51/12
See application file for complete search history.

(56) References Cited

U.S. PATENT DOCUMENTS

| | | |
|---|---|---|
| 2,152,852 A | 4/1939 | Loder |
| 2,285,448 A | 6/1942 | Loder |

(Continued)

FOREIGN PATENT DOCUMENTS

| | | |
|---|---|---|
| CN | 103086346 A | 5/2013 |
| DE | 3133353 A1 | 3/1983 |

(Continued)

OTHER PUBLICATIONS

Alvaro, M., et al., Single-step preparation and catalytic activity of mesoporous MCM-41 and SBA-15 silicas functionalized with perfluoroalkylsulfonic acid groups analogous to Nafion, 2004, Chemical Communications, (8), pp. 956-957 (Year: 2004).*
(Continued)

*Primary Examiner* — Yate' K Cutliff
(74) *Attorney, Agent, or Firm* — BakerHostetler

(57) ABSTRACT

A catalyst system for a liquid phase carbonylation reaction comprising a homogeneous acid catalyst component and a porous solid component, in particular for use in the formation of glycolic acid by carbonylation of formaldehyde. The homogeneous acid catalyst component is, for instance, sulphuric acid while the solid component can be unfunctionalized silica. A process for the carbonylation of an aldehyde to form a carboxylic' acid or derivative thereof is also
(Continued)

described. The process comprises the steps of contacting the catalyst with carbon monoxide, water and the aldehyde.

18 Claims, 3 Drawing Sheets

(51) Int. Cl.
    *C07C 51/12*     (2006.01)
    *B01J 35/10*     (2006.01)

(52) U.S. Cl.
    CPC ....... *B01J 35/1023* (2013.01); *B01J 35/1038* (2013.01); *B01J 35/1042* (2013.01); *B01J 35/1061* (2013.01); *C07C 51/12* (2013.01); *B01J 2229/37* (2013.01)

(56) References Cited

U.S. PATENT DOCUMENTS

| | | | |
|---|---|---|---|
| 2,443,482 | A | 6/1948 | Shattuck |
| 3,754,028 | A * | 8/1973 | Lapporte ............... C07C 51/12 562/518 |
| 3,911,003 | A | 10/1975 | Suzuki |
| 4,016,208 | A | 4/1977 | Suzuki |
| 4,052,452 | A | 10/1977 | Scardigno et al. |
| 4,087,470 | A | 5/1978 | Suzuki |
| 4,136,112 | A | 1/1979 | Bakshi |
| 4,140,866 | A | 2/1979 | Nielsen |
| 4,188,494 | A | 2/1980 | Suzuki |
| 4,431,486 | A | 2/1984 | Balmat |
| 5,420,093 | A | 5/1995 | Joly et al. |
| 5,731,256 | A | 3/1998 | Benazzi et al. |
| 6,376,723 | B2 | 4/2002 | Drent et al. |
| 7,045,481 | B1 * | 5/2006 | Parasher ............... B01J 27/053 502/102 |
| 8,299,297 | B2 * | 10/2012 | Sun ........................ B01J 29/166 562/518 |
| 2010/0290962 | A1 | 11/2010 | Wilson et al. |
| 2013/0261333 | A1 * | 10/2013 | Barnicki ............... C07C 29/149 562/518 |

FOREIGN PATENT DOCUMENTS

| | | | |
|---|---|---|---|
| EP | 0114657 | * 1/1984 | ............ C07C 51/12 |
| EP | 0114657 A1 | 8/1984 | |
| EP | 1360222 A1 | 11/2003 | |
| EP | 1786850 A1 | 5/2007 | |
| GB | 1499245 A | 1/1978 | |
| JP | 56073042 | 6/1981 | |
| JP | 2503178 | 8/1994 | |
| KR | 1995009480 | 8/1994 | |
| KR | 19950011114 | 9/1995 | |
| KR | 0124821 | 12/1997 | |
| KR | 1995011378 | 11/1998 | |
| KR | 19950013078 B1 | 11/1998 | |
| KR | 0155273 | 12/1998 | |
| WO | WO92005138 | 4/1992 | |
| WO | WO2002/055587 A1 | 7/2002 | |
| WO | WO2006/013060 A1 | 2/2006 | |
| WO | WO2006013080 A1 | 2/2006 | |
| WO | WO2007090676 A1 | 8/2007 | |
| WO | WO2009/140787 A1 | 11/2009 | |
| WO | WO2009140788 A1 | 11/2009 | |
| WO | WO2009140850 A1 | 11/2009 | |

OTHER PUBLICATIONS

Bossaert, W. D., et al., Mesoporous sulfonic acids as selective heterogeneous catalysts form the synthesis of monoglycerides, 1999, Journal of Catalysis, 182, pp. 156-164 (Year: 1999).*
Corma, A., et al., Silica-Bound homogeneous catalyst as recoverable and reusable catalyst in organic synthesis, 2006, Adv. Synth. Catal., 348, pp. 1391-1412 (Year: 2006).*
Diaz, I., et al., Synthesis, characterization and catalytic activity of MCM 141-type mesoporous silicas fictionalized with sulfonic acid, 2001, Applied Catalysis A: General, 2005, pp. 19-30 (Year: 2001).*
Rhijn, W. V., et al., Sulfonic acid bearing mesoporous materials as catalysts in furan and polyol derivatization, 1998, Mesoporous Molecular Sieves, Studies in Surface Science and Catalysis, vol. 117, pp. 183-190 (Year: 1998).*
Yuan, X., et al., Perodic mesoporous organosilicas functionalized with sulfonic acid group. Synthesis and alkylation of phenol, 2003, Chemistry Letters, vol. 32, No. 7, pp. 650-651 (Year: 2003).*
He et al., Condensation of Formaldehyde and Methyl Formate to Methyl Glycolate and Methyl Methoxy Acetate Using Heteropolyacids and Their Salts, Catalysis Today, vol. 51, Issue 1, Jun. 1999, pp. 127-134.
Lee et al., "Carbonylation of Formaldehyde Over Ion Exchange Resin Catalysts, 1. Batch Reactor Studies," Industrial & Engineering Chemistry Research, American Chemical Society, vol. 32, No. 2, Feb. 1, 1993.
GB1605062.7 Combined Search and Examination Report dated Oct. 31, 2016.
PCT/GB2016/050860 International Search Report dated Aug. 9, 2016.
PCT/GB2016/050860 Written Opinion dated Aug. 9, 2016.

\* cited by examiner

US 10,335,774 B2

CARBONYLATION PROCESS AND CATALYST SYSTEM THEREFOR

CROSS-REFERENCE TO RELATED APPLICATIONS

This application is the National Stage of International Patent Application No. PCT/GB2016/050860 filed Mar. 24, 2016, which claims priority from Great Britain Patent Application No. 1505977.7 filed Apr. 8, 2015, the disclosures of each of which are incorporated herein by reference in their entirety.

TECHNICAL FIELD

The present invention relates to a catalyst system. More particularly it relates to a catalyst system for use in a process for the production of glycolic acid. In a second aspect of the present invention, it relates to a process for the production of an acid, in particular glycolic acid using the catalyst system.

BACKGROUND

The reaction to form glycolic acid by the carbonylation of formaldehyde with carbon monoxide and water using strong acid catalysts is well known. The basic process was first disclosed by DuPont in U.S. Pat. No. 2,152,852. The process was for the preparation of glycolic acid in the liquid phase by reacting formaldehyde, water and carbon monoxide in the presence of a homogeneous acidic catalyst at temperatures between 50° C. and 350° C. and at a pressure between 5 and 1500 atma. Sulfuric acid, hydrochloric acid, phosphoric acid, boron fluoride, formic acid and glycolic acid are identified as being suitable catalysts.

DuPont went on to obtain further patents in this field, including, U.S. Pat. No. 2,285,448 which related to the hydrogenation of glycolic acid to ethylene glycol, and U.S. Pat. No. 2,443,482 which related to a continuous process for formaldehyde carbonylation.

The process for producing ethylene glycol was commercialised and operated by DuPont until the late 1960's when this route to ethylene glycol became uncompetitive. The plant was then operated for the production of glycolic acid in which sulfuric acid was used as catalyst at a temperature of 200° C. and at a pressure of from 400 to 700 bar.

The processes described in these initial cases suffered from numerous problems. These problems included those attributable to the need to operate at very high pressure. In addition, the selectivity was poor. It was also necessary to contend with the highly corrosive reaction mixture and the difficulty of removing the homogeneous acid catalyst such as sulfuric acid from the reaction product.

Various proposals have been made to address some or all of these problems. For example, U.S. Pat. No. 3,859,349 attempts to address the problems associated with separating the sulphuric acid catalyst and suggests using ion exchange resins as an alternative to neutralisation with calcium carbonate, which had been the previous approach. However, the sulfonic acid based ion exchange resins have limited thermal stability in aqueous environments leading to the loss of acid groups.

Another proposal was that described in U.S. Pat. No. 4,431,486 in which azeotropic distillation of the crude glycolic acid product was proposed as a means of reducing the water content in the recycle to the carbonylation reactors thereby minimising byproduct formation and increasing the yield from the feed formaldehyde.

Another approach has been to look at alternative catalyst systems as a means of reducing the reactor operating pressure. Hydrogen fluoride has been suggested as being a suitable catalyst in U.S. Pat. Nos. 3,911,003, 4,016,208, 4,087,470, 4,136,112 and 4,188,494. Processes which use hydrogen fluoride in place of sulfuric acid as catalyst are suggested to allow operating pressures of 1 to 275 bar.

A further alternative process is disclosed in U.S. Pat. No. 4,052,452 in which Cu(I) or Ag salts in concentrated sulfuric acid are suggested as a means of increasing the carbon monoxide solubility and it is suggested that this enables the operating pressure to be reduced to between 0.1 and 30 atma. Whilst this may address the operating pressure issues, such systems are extremely sensitive to poisoning by water and separation and recycle of the metallic catalyst is difficult.

In U.S. Pat. No. 6,376,723 it is proposed that the reaction should be conducted with an acid catalyst having a pKa value of less than −1 in the presence of a sulfone as a means of moderating the reaction conditions. There is also a suggestion that heterogeneous catalysts could be used.

U.S. Pat. No. 4,140,866 looks at the problems associated with removing the sulfuric acid catalyst from glycolic acid produced by formaldehyde carbonylation. The proposed solution is to first treat the reaction mixture with an alkali metal hydroxide to form the dissolved sulfate salt and this is then precipitated on esterification of the glycolic acid with ethylene glycol and removal of water.

A widely adopted strategy for overcoming the problems associated with separating homogeneous catalysts from reaction mixtures is to replace the homogeneous catalysts with heterogeneous catalysts that can easily be mechanically separated. Several solid acid materials have been suggested as suitable catalysts for formaldehyde carbonylation. These include sulfonic acid ion exchange resins, aluminosilicate zeolites, polyoxometalate salts and alkyl sulfonic acid polysiloxanes.

The use of solid insoluble particulate acidic catalysts having a hydrogen ion exchange capacity in excess of 0.1 milliequivalents per gram was first described in GB1499245. Sulfonic acid based ion-exchange resins, acid clays and zeolites are listed as suitable catalysts. Strongly acidic cation exchange resins in a reaction solvent such as acetic acid are suggested in JP56073042A2 and the use of FZ-1 and ZSM type zeolites in EP0114657.

An alternative process for the preparation of glycolic acid or its esters is disclosed in DE3133353C2. In this process, formaldehyde is reacted with carbon monoxide and water or an alcohol in an inert diluent in two reaction steps. In the first step, formaldehyde is reacted with carbon monoxide using an acidic, solid, insoluble, finely distributed catalyst at a ratio of hydrogen ion exchange capacity of the catalyst to the molar amount of the formaldehyde of 1:1 to 5:1, a temperature of 30° C. to 200° C. and a pressure of 10 to 325 bar. In the second step, water or an alcohol having 1 to 20 carbon atoms is added at a temperature of 20° C. to 200° C. and a pressure of 1 to 325 bar. The catalyst is subsequently mechanically separated from the reaction medium.

KR19950013078B1 relates to a process for producing glycolic acid in which formaldehyde and carbon monoxide are reacted in the presence of water or water-methanol mixture using a heterogeneous solid catalyst, which is polymeric strong acid catalyst ion-exchanged by 5-40 wt % with monovalent metal of Group IB in a water-soluble inert solvent. Dioxane is used as a water-soluble inert solvent.

A similar process is described in KR19950013079B1 in which formaldehyde and carbon monoxide are reacted in the presence of water or water-methanol mixture using a polymeric strong acid catalyst in a water-soluble inert solvent.

A process for continuously manufacturing methyl glycolate from formaldehyde, carbon oxide and methanol is described in KR19950009480B1 in which a flow reactor filled with a polymeric strong acid catalyst is used. Reactant mixture of formaldehyde, water and inert solvent and carbon monoxide is supplied to the upper part of the reactor, and methanol is supplied to the lower part. In the upper part of the reactor, glycolic acid is produced via acid catalysis. In the lower part of the reactor, methyl glycolate is prepared from methanol and formed glycolic acid. The pressure of carbon monoxide is 500 to 6,000 psig and the temperature is 80 to 200° C. The suggested selectivity for this one-step procedure is relatively high.

KR0124821B1 relates to separating methylglycolate from an acidic solution. In this case, the reaction solution formed by a carbonylation reaction and an esterification reaction contains methyl glycolate, dioxane, water, methanol and hydrogen ion. This reaction solution is sent to a neutralization reactor and is neutralized by the addition of alkali to give a salt. The reaction solution containing salt is distilled to separate methanol, water and dioxane from methyl glycolate, salt and dioxane. The methanol separated from dioxane is recirculated to the carbonylation reactor. The solution which separated from the lower part of the distillation tower contains methyl glycolate, salt and dioxane. This is sent to a solid-liquid separator to separate the methyl glycolate from the solvent.

A further process for the production of methyl glycolate is described in KR19950011114B1. In this process formaldehyde is reacted with carbon monoxide to make a glycolic acid. The glycolic acid is then reacted with methanol to make a methyl glycolate. Residual formaldehyde is then reacted with methanol to make methylal. The methyl glycolate and methylal are then separated by distillation. The methylal is reacted with a Fe—Mo catalyst to return it to formaldehyde which is then recovered and concentrated before being recycled.

An alternative heterogeneous acid catalyst for the formaldehyde carbonylation reaction is described in U.S. Pat. No. 6,376,723. Sulfonic acid based ion exchange resins such as Amberlyst 38W and Nafion SAC13 are mentioned as suitable commercially available catalysts. Deloxan ASP 1/9, an alkyl sulfonic acid polysiloxane, is also listed as a suitable catalyst. This material is formed by co-polycondensation of propyl(3-sulfonic acid)siloxane and $SiO_2$.

He et al, in Catalysis Today, 51 (1999), 127-134, describe the use of heteropolyacids as homogeneous catalysts for the condensation of formaldehyde and methyl formate.

A still further process is described in JP2503178. In this process, glycolic acid is formed by hydrolysis of polyglycolide made from formaldehyde and carbon monoxide in the presence of a solid heteropoly acid.

WO2009/140787, WO2009/140788 and WO2009/140850 relate to processes using insoluble polyoxometalate compounds. These compounds either have specific acid properties or are encapsulated within zeolite cages, as solid acid catalysts, to produce glycolic acid from carbon monoxide and formaldehyde. However, the metal salts are prone to leaching of the metal component, which will reduce the number of active acid sites. In the case of zeolite impregnated with polyoxometalate salts, acid leaching will impact both the zeolite substrate and the salts themselves.

There are also a number of cases relating to various substituted organopolysiloxane compounds and their uses. These cases can be grouped into five families which cover different classes of polysiloxane compounds. The five groupings can be typified by: EP1360222B1, EP1786850B1, WO2006/013080A1, WO2007/090676A1 and US2010/0290962A1 which disclose various families of compounds. These documents suggest that these compounds may be useful for carbonylation reactions, but there is no detailed teaching as to how these materials can be used as catalysts for formaldehyde carbonylation in particular or to carbonylation reactions more generally.

It has been suggested that the use of heterogeneous catalysts will reduce the corrosion of the reaction system. None of the heterogeneous catalysts proposed in the prior art has been adopted commercially.

Although there have been numerous patents and publications relating to the production of ethylene glycol from glycolic acid which is formed by carbonylation of formaldehyde, there remains a need for an improved process which can compete economically with the established industrial production route.

The various approaches to trying to solve the problems associated with the reaction can be summarised into two categories. The first relates to the investigation of homogeneous catalyst systems which operate at lower pressure and lower acid concentration than has previously been achievable.

The second relates to the investigation of heterogeneous solid acid catalysts as these benefit from easier separation of the catalyst and reduced reactor corrosion. However, the solid catalysts proposed to date have also proved to have a number of shortcomings and have not been adopted commercially. These catalysts generally lack the thermal and chemical stability required to withstand the severe reaction conditions.

For example, aluminosilicate zeolites are not stable under highly acidic conditions, as the aluminium is leached from the structure causing it to collapse. This results in loss of activity and eventually complete disintegration of the catalyst (Pan et al, 1994, Studies in Surface Science and Catalysis). With a view to avoid this problem, it is proposed in EP0114657 that the reaction should be operated such that the amount of acid formed is limited, but this reduces the efficiency of the reactor and exacerbates separation problems.

It is well known that sulfonic acid based ion exchange resins have limited thermal stability in aqueous environments leading to a loss of acid groups. Furthermore it has been found that formaldehyde attacks the aromatic rings within styrene/di vinyl benzene based resins causing swelling and further loss of acid groups.

There has also been a suggestion that substituted organopolysiloxane compounds, such as Deloxan ASP 1/9, Quadrasil—SA and Silicycle (SCX-2), and alkyl sulfonic acid polysiloxanes, can be used but these have been found to quickly lose catalytic performance at effective process conditions. This has been attributed to the loss of the tethered organic acid groups due to hydrolysis.

SUMMARY

There therefore remains a need to provide catalytic systems with sufficient performance to make the production of ethylene glycol via the carbonylation of formaldehyde to glycolic acid economically viable. It is also expected that these catalytic systems will be suitable for use in other carbonylation reactions including hydrocarbonylation reactions and will address corresponding problems associated with these reactions. In investigating the problem of solid acid catalyst stability in the formaldehyde carbonylation environment a large number of materials have been tested. In the course of this testing, it was surprisingly observed that materials having a higher porosity than those with the same surface area had an enhanced activity when a homogeneous acid was also used. This was observed for solid acid catalysts whether they were non-functionalised silica solid, other non-functionalised solids such as activated carbon as well as the original polysolixane. Further, the catalytic effect was surprisingly greater than would be expected from the equivalent acid concentration in the liquid phase or that of the solid alone.

DETAILED DESCRIPTION OF ILLUSTRATIVE EMBODIMENTS

Thus according to a first aspect of the present invention there is provided a catalyst system for a liquid phase carbonylation reaction comprising a homogeneous acid catalyst component and a porous solid component.

The catalyst system of the present invention is particularly suitable for the formation of glycolic acid or derivatives thereof by the carbonylation of formaldehyde with carbon monoxide and water. Derivatives of glycolic acid include glycolic acid dimers, esters of glycolic acid, and if an alcohol is present, ester related adducts. The water may be added separately and/or the formaldehyde may be provided as an aqueous solution.

Without wishing to be bound by any theory, it is postulated that the enhanced effect is caused by interaction of the homogeneous acid and the surface of the solid support leading to higher active catalytic conditions which are responsible for the increased system activity or formaldehyde conversion. It may be considered that a pseudo-heterogeneous catalyst is formed. The catalyst system of the present invention may be considered as forming a temporary catalyst in-situ in the pores.

Any suitable homogeneous acid catalyst may be used as a component of the catalyst system of the present invention. Examples include sulfuric acid, triflic acid, sulfonic acids such as methylsulfonic acid, ethanesulfonic acid, p-toluenesulfonic acid, and perfluorooctanesulfonic acid and phosphorous based acids such as phosphonic acid and ethylphosphonic acid. In addition, compositions modified with groups to enhance interaction with the solid component may be used. Examples include trihydroxysilylpropane sulfonic acid, alkyl phosphonic acid, and trihydroxysilylethylsulfonic acid. In another arrangement, formic acid may be used.

Any suitable solid component may be used provided that it is porous and stable to the reaction environment. Any suitable pore size can be used. In one arrangement it may have a surface area of from about 250 to about 900 $m^2/g$ and a pore volume of from about 0.2 to 1 cc/g. A surface area of from about 400 to about 750 m2/g or from about 500 to about 600 m2/g may be used.

Although the solid component may be selected to have some catalytic activity in the absence of the homogeneous component, the combined catalytic effect of the solid component and the homogeneous catalyst surprisingly will be greater than that expected from the components individually.

In one arrangement, the solid component may be unfunctionalised. By "unfunctionalised" we mean that the surface has not been specifically modified to add active catalytic moieties to the surface. In one arrangement the unfunctionalised solid component may have hydroxyl groups located on the surface thereof.

In a second arrangement, the solid component may be a functionalised material. By "functionalised" we mean that the material has been modified to have enhanced activity. In one arrangement, the functionalization may be to add alkyl sulfonic acid groups, hydroxyl groups or both alkyl sulfonic acid groups and hydroxyl groups on the surface of the material, in the pores of the solid component or on both the surface and in the pores.

Without wishing to be bound by any theory it is believed that in some arrangements, the homogeneous component temporarily interacts with the surface of the solid component while reaction occurs, it is then released and is free to re-attach at another site where it can take further part in the reaction. Where hydroxyl groups and/or alkyl sulfonic acid groups are present, the interaction may occur at these sites.

Examples of suitable solid components include silicas, activated carbons, ordered mesoporous carbon, nanoporous carbons, some titanias and zirconias. The silicas may be those from the Johnson Matthey QuadraSil range including SA, TA, AP or MP or QuadraSil PHI available from Sigma Aldrich. Other suitable supports include synthesised ordered mesoporous (or nanoporous) carbons having ordered silica frameworks such as MCM-41, MCM-48, SBA-51, KIT-6, and IITM-56 as templates.

Any suitable amount of homogeneous acid catalyst component may be present in the catalyst system. In one arrangement it may be from: about 10 ppm to about 25 wt %; from about 50 ppm to about 20 wt %; from about 1 wt % to about 15 wt %; or from about 2 wt % to about 10 wt %. The ppm in the solution is ppm weight of acid One benefit of the present invention is that the acid loading of the catalyst system can be varied during operation to enable the activity in the reactor to be adjusted as required.

According to a second aspect of the present invention there is provided a process for the carbonylation of an aldehyde to form a product acid or derivatives thereof comprising the steps of contacting the catalyst of the above first aspect with carbon monoxide, water and the aldehyde.

In a preferred arrangement, the process is for the production of glycolic acid or a derivative thereof by the reaction of carbon monoxide, water and formaldehyde.

The water may be present in any suitable amount. It may be used in an amount from the stoichiometric requirement to a molar ratio of about 4:1 water:formaldehyde.

The water may additionally act as the solvent for the reaction. Where water is used as a solvent it will be used in an amount in excess of the ratio detailed above. The water may be provided separately. Alternatively or additionally it may be supplied in the aldehyde feed or with another solvent.

Alternatively the water may be present in an amount which is sufficient for the reaction and a separate solvent may be used.

Where a solvent is to be used, any suitable solvent may be used. Suitable solvents include carboxylic acids such as acetic acid, propionic acid, butyric acid or the like. The solvent used may be the acid that is being produced in the reaction and thus it may be the glycolic acid. In this arrangement, the acid may be recycled acid. Polyglycolide may also be used.

Alternative solvents may also be used and include sulphanones such as 2,3,4,5-tetrahydrothiophene-1,1-dioxide.

Aldehyde reactant, such as the formaldehyde, can be supplied as a solution in water or generated in situ within the reactor. For example, in one embodiment of the invention, paraformaldehyde is used as a reactant. Paraformaldehyde is a polymer of formaldehyde, which reverts to monomeric formaldehyde in the presence of polar molecules, such as water or alcohol solvents. In another embodiment, formaldehyde may be supplied in the form of a dialkoxymethane derivative that can hydrolyse to formaldehyde in the reactor.

The carbon monoxide can be a pure source of carbon monoxide, optionally comprising small quantities of impurities such as one or more of light alkanes, carbon dioxide or hydrogen. Alternatively, the carbon monoxide source can be a component of a gaseous mixture, for example synthesis gas (syngas) which is a mixture of hydrogen and carbon monoxide.

Reaction conditions will depend on the reaction being conducted. For the production of glycolic acid, the temperature is typically in the range of from about 50° C. to about 400° C., for example in the range of from about 100° C. to about 250° C. and the pressure at which reaction is carried out is typically in the range of from about 1 to about 1000 bara (about 0.1 to about 100 MPa), such as in the range of from 10 to 200 bara (0.1 to 20 MPa).

The process can be carried out in any suitable manner. In one arrangement it may be conducted in a continuous flow configuration in which carbon monoxide, aldehyde, water, acidic homogeneous catalyst component and optional solvent, either pre-mixed or separately, are introduced to a fixed bed or slurry reactor containing the solid catalyst component to produce a product composition which is continuously withdrawn from the reactor. The reaction can take place in single or multiple reactors which may be of different types arranged in either series or parallel configuration. One or more of the feedstocks may be added at a single point or sequentially as the reaction progresses.

In one alternative arrangement, the reaction can be conducted batch-wise. In one embodiment this involves suspending and stirring a suspension of the solid catalyst component in a liquid reaction composition comprising a homogeneous acid catalyst, solvent and aldehyde, with carbon monoxide being fed into the reactor under pressure. The resulting product composition can then be periodically removed from the reactor. Typically, any catalyst being removed from the reactor with the product stream is separated and fed back to the reactor to minimise catalyst loss.

Howsoever formed, the product stream recovered from the reactor comprises the desired acid. The product stream can be treated to recover one or more of the solvent, unreacted reactants and the homogeneous catalytic component, for example formaldehyde and carbon monoxide. This can be achieved by a variety of means. For example, formaldehyde and carbon monoxide can be recovered by flash separation and/or distillation.

The present invention will now be described by way of example with reference to the following examples and figures.

COMPARATIVE EXAMPLE 1

An aqueous solution of formaldehyde was passed to a fixed bed reactor charged with a silica catalyst functionalised with trihydroxysilylethylsulfonic acid where it was contacted with carbon monoxide. The reactor was operated at a temperature of 160° C., a pressure of 170 barg, a formaldehyde flow rate of 150 mL/h and a gas flow of 50 L/h.

Figure 1:
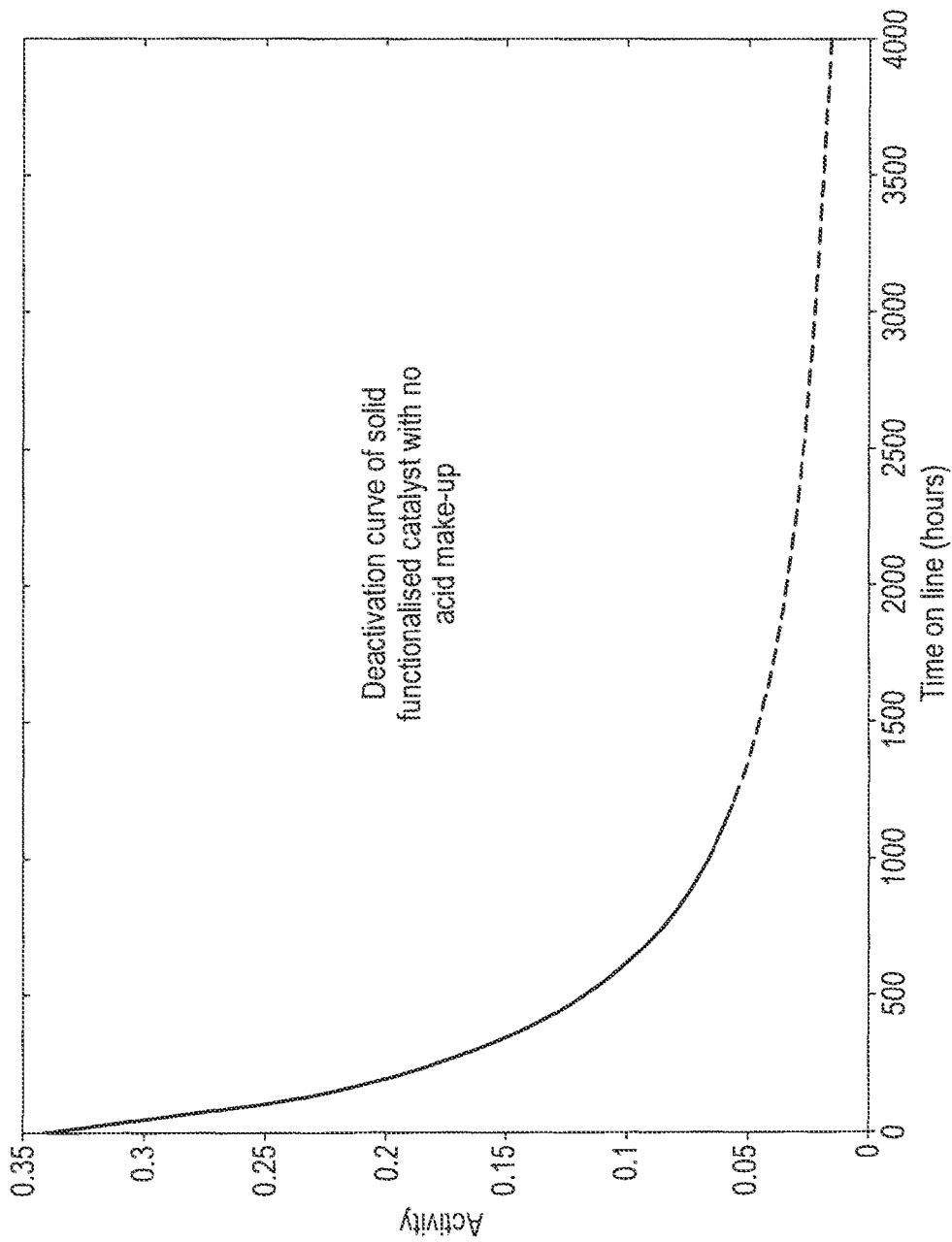
FIG. 1 is a graph illustrating the results of Comparative Example 1.

Initially reaction occurred and glycolic acid was produced. The initial catalyst activity was calculated to be in the region of 0.3 to about 0.35, as illustrated in FIG. 1, the catalyst deactivated. Without wishing to be bound by any theory it is postulated that the functionalization is removed as the reaction continues such that after about 1000 hours there is effectively only silica present although practically there may be some of the silica that still is functionalised albeit with low effective catalytic activity.

The catalyst activity number is an assessment of the activity of the catalyst taking a variety of factors into consideration including conversion and yield. The same method of assessing catalyst activity was utilised for all examples and therefore the values can be considered as empirical values allowing a direct comparison of results.

COMPARATIVE EXAMPLE 2

Comparative Example 1 was repeated. However, the silica catalyst was replaced with sulfuric acid as catalyst. The reaction was carried out over a bed of glass balls which it will be understood are a non-porous support.

Figure 2:
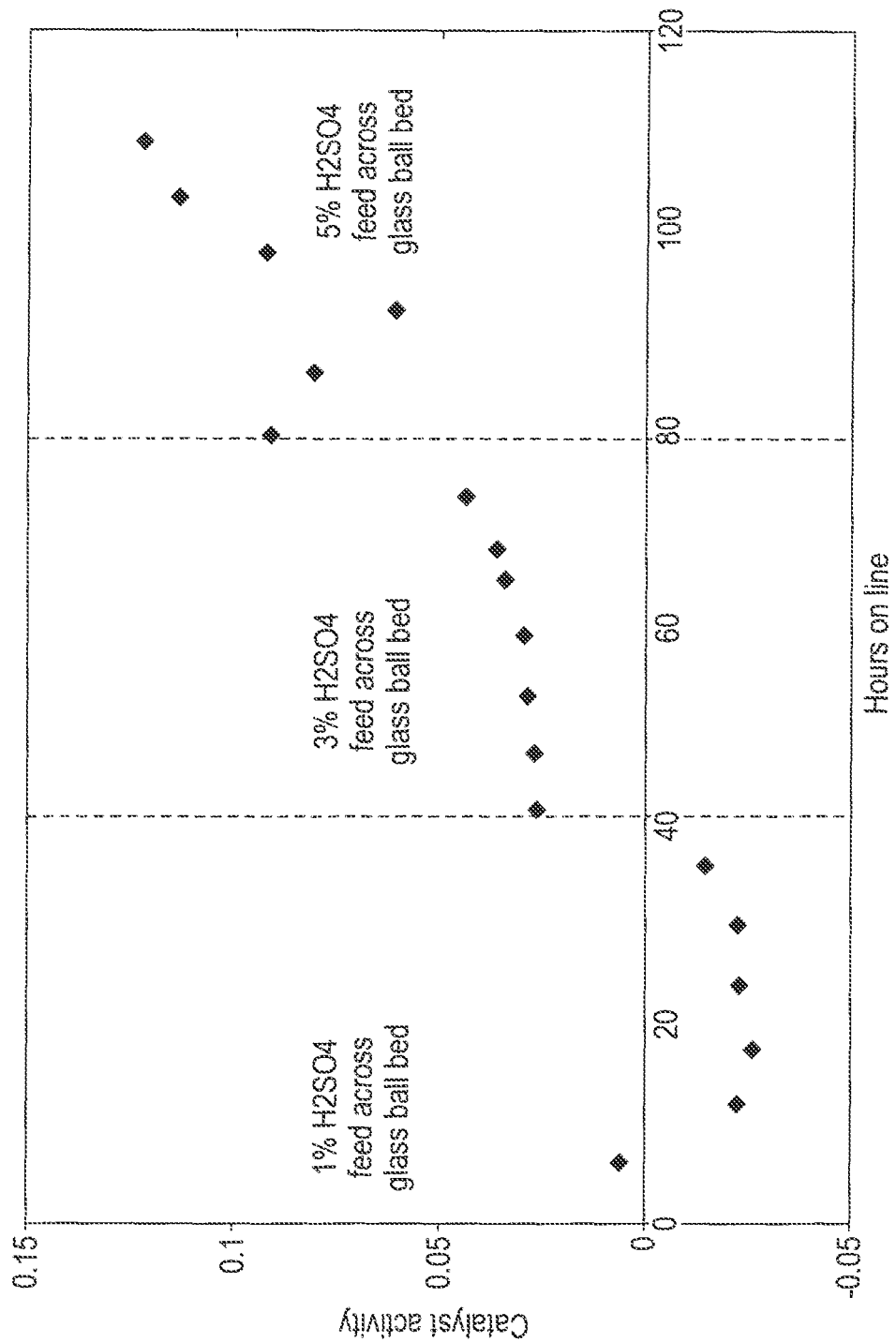
FIG. 2 is a graph illustrating the results of Comparative Example 2.

As illustrated in FIG. 2, the amount of sulfuric acid was varied with time. When the amount of sulfuric acid is above about 5 wt %, the catalyst activity was adequate for reaction but the catalyst activity was only around 0.1.

EXAMPLE 1

Figure 3:
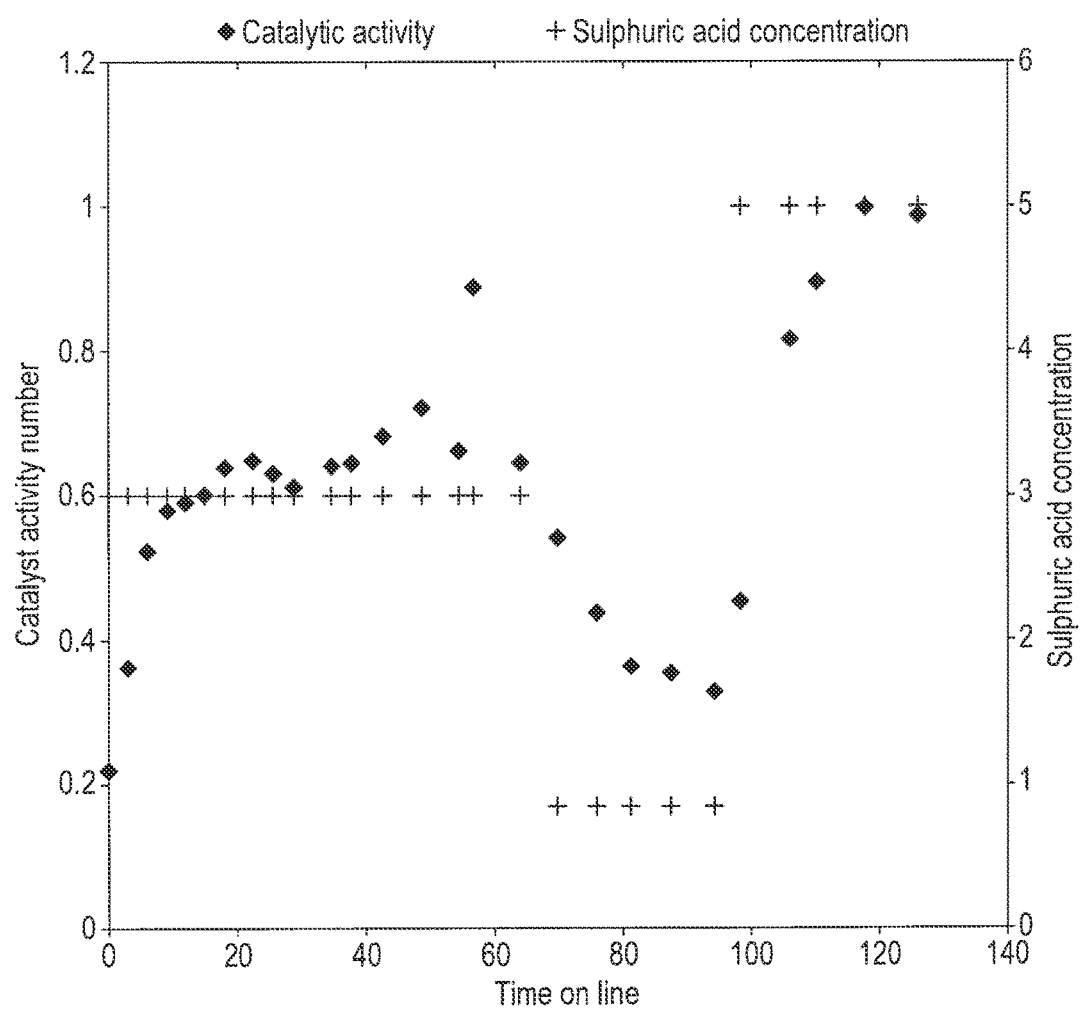
FIG. 3 is a graph illustrating the results of Example 1.

Comparative Example 1 was repeated except that the catalyst was replaced with a catalyst system comprising an unfunctionalised porous silica support and a sulfuric acid catalyst. Typical physical properties of the material include 0.98 cm$^3$/g pore volume, 2.1 to 2.7 nm pore size and a surface area of 500 to 1000 m$^2$/g (BET). As illustrated in FIG. 3, whilst the catalyst activity did vary with the sulfuric acid concentration, the combination of the porous support and the liquid catalyst resulted in a catalyst activity significantly higher than was achieved in either Comparative Examples 1 or 2.

It is therefore clear that the interaction between the porous support and the liquid acid provides an improvement which is not observed when a non-porous support such as glass balls is used.

The invention claimed is:

1. A catalyst system for a liquid phase carbonylation reaction comprising:
   a homogeneous acid catalyst selected from sulphuric acid, triflic acid, sulfonic acids, alkyl phosphonic acids, phosphoric acid, and formic acid;
   and,
   a porous solid component.

2. The catalyst system according to claim 1, wherein the homogeneous acid catalyst is a sulfonic acid that is selected from methylsulfonic acid, ethanesulfonic acid, p-toluenesulfonic acid, perfluorooctanesulfonic acid, trihydroxysilylpropane sulfonic acid, and trihydroxysilylethylsulfonic acid.

3. The catalyst system according to claim 1, wherein the solid component has alkyl sulfonic acid groups, hydroxyl groups, or both alkyl sulfonic acid groups and hydroxyl groups on a surface of the solid component, in pores of the solid component, or on both a surface and in pores of the solid component.

4. The catalyst system according to claim 3, wherein the solid component is a porous silica material.

5. The catalyst system according to claim 1, wherein the solid component has a surface area of from about 250 to about 900 $m^2/g$ and a pore volume of from about 0.2 to 1 cc/g.

6. The catalyst system according to claim 1, wherein the amount of homogeneous acid catalyst component present in the catalyst system is from: about 10 ppm to about 25 wt %; from about 50 ppm to about 20 wt %; from about 1 wt % to about 15 wt %; or from about 2 wt % to about 10 wt %.

7. A process for the carbonylation of an aldehyde to form a carboxylic acid or derivative thereof comprising the steps of contacting the catalyst system of claim 1 with carbon monoxide, water, and the aldehyde.

8. The process according to claim 7 for the production of glycolic acid by the reaction of carbon monoxide, water, and formaldehyde.

9. The process according to claim 8, wherein the water is present in an amount from the stoichiometric requirement to a molar ratio of about 4:1 water:formaldehyde.

10. The process according to claim 8, wherein the reaction is carried out in the presence of a solvent.

11. The process according to claim 10, wherein the solvent is, water, a carboxylic acid, or a sulfone.

12. The process according to claim 10, wherein the solvent is glycolic acid or polyglycolide.

13. The process according to claim 8, wherein the process is carried out at a temperature of from about 50° C. to about 400° C.

14. The process according to claim 8, wherein the process is carried out a pressure of from about 1 to about 1000 bara.

15. The process according to claim 8, wherein the amount of homogeneous acid catalyst component present in the catalyst system may be varied during the process.

16. The process according to claim 8, wherein the process is carried out in a continuous flow configuration or batchwise.

17. The process according to claim 8, wherein the process is carried out at a temperature of from about 100° C. to about 250° C.

18. The process according to claim 8, wherein the process is carried out a pressure of from about 10 to 200 bara.

* * * * *